(12) United States Patent
Castellarnau

(10) Patent No.: US 8,568,595 B2
(45) Date of Patent: Oct. 29, 2013

(54) METHOD AND DEVICE TO EARLY PREDICT THE KT/V PARAMETER IN KIDNEY SUBSTITUTION TREATMENTS

(75) Inventor: Alex Castellarnau, Melsungen (DE)

(73) Assignee: B. Braun Avitum AG, Melsungen (DE)

( * ) Notice: Subject to any disclaimer, the term of this patent is extended or adjusted under 35 U.S.C. 154(b) by 315 days.

(21) Appl. No.: 13/063,533

(22) PCT Filed: Sep. 15, 2009

(86) PCT No.: PCT/EP2009/006653
§ 371 (c)(1),
(2), (4) Date: Mar. 29, 2011

(87) PCT Pub. No.: WO2010/028860
PCT Pub. Date: Mar. 18, 2010

(65) Prior Publication Data
US 2011/0163034 A1    Jul. 7, 2011

(30) Foreign Application Priority Data
Sep. 15, 2008  (EP) .................................... 08016171

(51) Int. Cl.
*B01D 61/32* (2006.01)
*B01D 61/28* (2006.01)
*A61M 1/16* (2006.01)

(52) U.S. Cl.
USPC ............... 210/646; 210/85; 210/86; 210/97; 210/143; 210/321.65; 210/739; 210/745; 210/746; 604/4.01; 604/5.04; 604/6.09; 604/29; 604/30; 604/503; 700/266

(58) Field of Classification Search
USPC ............ 210/645, 646, 739, 745, 746, 85, 86, 210/97, 109, 143, 321.65; 604/4.01, 5.01, 604/5.04, 6.08, 6.09, 6.11, 29, 30, 503; 700/266
See application file for complete search history.

(56) References Cited

U.S. PATENT DOCUMENTS 5,518,623 A * 5/1996 Keshaviah et al. ............ 210/646

FOREIGN PATENT DOCUMENTS

| EP | 1083948 | 3/2001 |
|---|---|---|
| WO | 9408641 | 4/1994 |
| WO | 9962574 | 12/1999 |

OTHER PUBLICATIONS

Fernandez et al., Dialysate-side urea kinetics. Neural network predicts dialysis dose duirng dialysis, Medical & Biological Engineering & Computing, vol. 41, No. 4, 2003, pl. 392-394.

(Continued)

Primary Examiner — John Kim
(74) Attorney, Agent, or Firm — RatnerPrestia

(57) ABSTRACT

A method for determining or predicting the adequacy parameters that will be achieved at the end of a kidney substitution treatment during said kidney substitution treatment wherein the kidney substitution treatment is provided by a machine, which has an extracorporeal blood system pumping the patient blood through the blood chamber of a dialyzer, wherein the dialyzing fluid collects the waste products from the patient after flowing through the dialyzing fluid chamber of the dialyzer and wherein a device able to measure a adequacy parameter is coupled with the kidney substitution treatment machine and wherein the slope of a preferable linear guideline for the adequacy parameter is compared to the slope of the delivered adequacy parameter and if the slope of both are equal a linearization is performed to determine or predict the adequacy parameter at the end of the kidney substitution treatment.

18 Claims, 3 Drawing Sheets

(56) References Cited

OTHER PUBLICATIONS

Canaud et al., "On-Line Dialysis Quantification in Actuel Ill Patients. Preliminary Clinical Experience With a Multipurpose Urea Sensor Monitoring Device", Asaio Journal, vol. 44, No. 3, 1998, pp. 184-190.

Depner et al.., "Solute Transport mechanisms in dialysis", Replacement of renal function by dialysis, 5th ed., Kluwer academic publishers, 2004, pp. 73-91.

Polaschegg et al., "On-line automatic intradialytic clearance measurement using conductivity", Replacement of renal function by dialysis, 5th ed., Kluwer academic publishers, 2004, pp. 414-418.

Fridolin et al., "On-line monitoring of solutes in dialysate using absorption of ultraviolet radiation: Technique descriptions," The Intl. Journal of Artificial Organs, vol. 25, No. 8, 2002, pp. 748-761.

Uhlin, "Haemodialysis Treatment Monitored On-Line by Ultra Violet Absorbance", Linkoping University, Medical Dissertations No. 962, Dept. of Medicine and Care Div. of Nursing Science & Dept. of Biomedical Engineering, 2006.

International Search Report for PCT/EP2009/006653 mailed Feb. 19, 2010.

* cited by examiner

METHOD AND DEVICE TO EARLY PREDICT THE KT/V PARAMETER IN KIDNEY SUBSTITUTION TREATMENTS

CROSS REFERENCE TO RELATED APPLICATIONS

This application is the U.S. national phase application of PCT International Application No. PCT/EP2009/006653, filed Sep. 15, 2009 which claims priority to European Patent Application No. EP 08016171.4 filed Sep. 15, 2008 the contents of such applications being incorporated herein by reference.

FIELD OF THE INVENTION

The invention relates to a method and a device to early predict the Kt/V parameter in kidney substitution treatments.

BACKGROUND OF THE INVENTION

Dialysis adequacy is the topic that has got and gets more attention when one thinks about patient outcome. In order to estimate dialysis adequacy one needs a parameter establishing a relation between dialysis dosage and patient outcome. The most accepted parameter to estimate the quantity of dialysis delivered or dosage is the Kt/V, where K is the effective clearance for urea, t is the treatment time and V is the urea distribution volume which matches the total body water.

The NCDS (National Cooperative Dialysis Study) and the HEMO study found, after analyzing a large patient group, that morbidity and mortality in end stage renal disease (ESRD) was strongly correlated with the Kt/V value or dialysis dose. Data obtained from these studies resulted in guidelines regarding hemodialysis treatments, which demand a minimum dose of Kt/V=1.2 for non-diabetic patients and 1.4 for diabetics (DOQI guidelines). It is worthy to point out that a morbidity decrease not only improves the patient well-being, but also reduces significantly the medical costs as the patient requires less care.

The need of a reliable and cost effective method to monitor the Kt/V and by extension control dialysis adequacy and morbidity, would therefore be easily understood to one of ordinary skill in the art from the description herein.

In the Kt/V calculation, the main problems are K and V estimation along with the multicompartment urea kinetics. V can be estimated by bioimpedance, anthropometric measurements or applying the urea kinetic model (UKM), all these methods have a certain degree of error. K can be estimated so far by measuring the urea blood concentration before and after the treatment or by monitoring inlet and outlet conductivity changes in the dialysate side.

Blood samples method is the reference one. After taking the blood samples and applying either UKM or Daugirdas formula a single pool Kt/V (spKt/V) is estimated, further, Daugirdas second generation formulas should be used to get an equilibrated Kt/V (eKt/V) which accounts for the urea rebound caused by the fact that urea kinetic's does not follow a single pool model but a multi-compartment one. This method has two main problems: it is not possible to know whether the treatment is adequate or not before it finishes, therefore it is not possible to perform any action to improve the situation; it is not an easy to apply method: sampling time is very important to get an accurate value, and the medical staff must send the samples to the lab, wait for the results and calculate Kt/V values with the help of a computer. These facts result on a monthly basis Kt/V measurements in best case, which means that in worst case scenario a patient might be under-dialyzed for one whole month.

Conductivity methods are based on the observation that sodium clearance is almost equal to urea clearance and that the relationship between dialysate conductivity and dialysate sodium concentration can be considered linear on the temperature range of interest. Therefore it is possible to get urea clearance by measuring the sodium diffusion transport through the membrane in the dialyzer.

It is important to introduce the concept of Dialysance, as it slightly differs from Clearance:

Clearance is defined as the ratio between transport rate and concentration multiplied by flow, and it is applicable when the diffusing substance is on the blood side but not on the dialysate, that is the case for urea.

Dialysance is defined as the ratio between transport rate and concentration gradient multiplied by flow, and it is applicable when the diffusing substance is in both dialyzer sides. When one applies conductivity methods to measure urea Clearance, one actually measures sodium Dialysance (see Depner T, Garred L. Solute transport mechanisms in dialysis. Hörl W, Koch K, Lindsay R, Ronco C, Winchester J F, editors. Replacement of renal function by dialysis, 5th ed. Kluwer academic publishers, 2004:73-91).

During conductivity based clearance measurements, a dialysate inlet conductivity different to the blood one is produced, which results in a net transfer of sodium either from blood to dialysate or from dialysate to blood due to the generated gradient. There are currently several methods which are applied in the industry:

In a first method a one-step conductivity profile is performed; in a second method a two-step conductivity profile is performed; and in a third method an integration of conductivity peaks is used. (see Polaschegg H D, Levin N W. Hemodialysis machines and monitoris. Hörl W, Koch K, Lindsay R, Ronco C, Winchester J F, editors. Replacement of renal function by dialysis, 5th ed. Kluwer academic publishers, 2004: 414-418). The main advantages of this approach is that it is relatively easy to implement and cost effective as it only needs an extra conductivity/temperature sensor downstream the dialyzer. It offers Kt/V measurements during the treatment allowing the medical staff to react and perform some actions in case the treatment is not going as it should. However, conductivity based methods have also some limitations: they can induce some sodium load in the patient during the measurement; they are not useful to obtain other interesting parameters like nPCR or TRU. The maximum measurement frequency offered so far by the industry is about 20 minutes, which means that in worst case scenario the patient could be under-dialyzed for 20 minutes. And although there are some publications claiming it, so far, conductivity methods haven't been applied with enough reliability to hemofiltration or hemodiafiltration treatments.

Another method to estimate hemodialysis adequacy is by direct measurement of the waste products (urea) concentration in the effluent dialysate, this method assumes that the evolution of urea concentration over the time in the dialysate side is proportional to the one in the blood, therefore the slope of the line obtained after applying the natural logarithm to the registered concentration values over the time will be the same on both sides: dialysate side and blood side. And by definition such slope is K/V, which multiplied by the therapy time results in the Kt/V value.

There are two different methods available to measure online the concentration of waste products in effluent dialysate: Urea sensors and UV spectrophotometry.

The limitations of the urea sensors are well known. Recent works carried out by Fridolin I. et al (see I. Fridolin, M. Magnusson, L.-G. Lindberg. On-line monitoring of solutes in dialysate using absorption of ultraviolet radiation: Technique description. The International Journal of Artificial Organs. Vol. 25, no. 8, 2002, pp. 748-761) and Uhlin F. (see Uhlin F. Haemodialysis treatment monitored online by ultra violet absorbance. Linköping University Medical Dissertations n° 962. Department of Medicine and Care Division of Nursing Science & Department of Biomedical Engineering. 2006.) have shown that UV spectrophotometry is a reliable and cost affordable method to monitor waste products in effluent dialysate. Additionally, the European Patent EP1083948B1 describes a sensor coupled with the dialysate flow system of a dialysis machine, which is actually an UV spectrophotometer measuring UV absorbance of UV absorbing products in spent dialysate.

Using any of the online measuring methods it is possible to know the delivered Kt/V at any treatment time, but it is not possible to predict with enough accuracy how much Kt/V will be delivered to the patient at the end of the dialysis session. Such information would be of great value for the physician in order to adjust the treatment parameters and improve the dialysis efficiency.

The delivered Kt/V by unit of time it is not constant during the treatment because of the multi-compartment nature of the urea kinetic model. During the dialysis treatment we can speak about two clearances, one between the dialysate and the extra cellular compartment, and another between intra and extra cellular compartment, which is smaller than the first one. On the first stage of the dialysis treatment the extra cellular compartment is quickly cleared, further on, the concentration decrease of waste products in blood slows down because the dialyzer clearance is limited by the clearance between compartments, in other words the uptake of waste products by the extra cellular from the intra cellular compartment is smaller than the dialyzer blood clearing capabilities. From the mathematical point of view it can be noticed by the fact that the ratio K/V decreases, thus the Kt/V by unit of time also decreases as the dialysis goes on.

The shortcomings of the methods measuring the clearance by means of conductivity have been already described, besides it linearizes the Kt/V along the whole dialysis treatment and introduce a prediction error because of both the low measurement frequency and the approximation of V.

When measuring Kt/V by means of the data delivered by any sensor or measuring device, which is able to continuously measure any waste product on spent dialysate, the high measuring frequency and the wealth of data allow to make an accurate prediction of the final Kt/V value.

SUMMARY OF THE INVENTION

Aspects of the invention are directed to providing a reliable method and device to determine or predict the final Kt/V value.

In accordance with one aspect of the present invention, a method is disclosed for determining or predicting the adequacy parameters that will be achieved at the end of a kidney substitution treatment during said kidney substitution treatment, wherein the kidney substitution treatment is provided by a machine, which has an extracorporeal blood system pumping the patient blood at a preset blood flow rate through the blood chamber of a dialyzer, which is divided by a semi-permeable membrane into the blood chamber and a dialyzing fluid chamber and wherein the dialyzing fluid flows at a preset flow rate through the dialyzing fluid system of the machine and collects the waste products from the patient after flowing through the dialyzing fluid chamber of the dialyzer and wherein a device able to measure continuously any kidney substitution treatment related waste product to deliver together with the data provided by the kidney substitution treatment machine a adequacy parameter wherein the device is coupled with the dialyzing fluid system of the kidney substitution treatment machine and wherein the slope of a preferable linear guideline for the adequacy parameter, which end at target adequacy parameter at the end of the kidney substitution treatment, is compared to the slope of the delivered adequacy parameter and if the slope of both are equal with the next delivered adequacy parameters a linearization is performed to determine or predict the adequacy parameter at the end of the kidney substitution treatment.

In accordance with another aspect of the present invention, a device is disclosed which is a kidney substitution treatment machine, wherein the method described herein is implemented, wherein the user can set a planned adequacy parameter at the end of the kidney substitution treatment and wherein an alarm or warning system is implemented to let the user know that the planned adequacy parameter at the end of the kidney substitution treatment will not be achieved.

Further goals, advantages, features and possibilities of use of this invention arise out of the subsequent description of the embodiments of the invention. Therefore every described or depicted feature of its own or in arbitrary meaningful combination forms the subject matter of the invention even independent of its summary in the claims or its reference to other claims.

BRIEF DESCRIPTION OF THE DRAWINGS

It shows.

DETAILED DESCRIPTION OF THE INVENTION

Aspects of the invention are now described with the help of a mathematical derivation.

Figure 1:
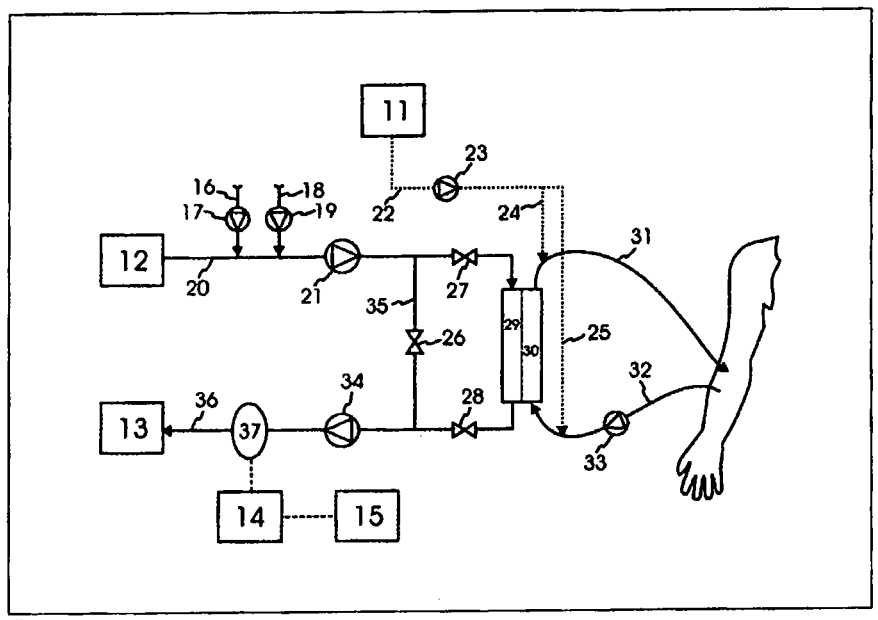
FIG. 1 Depicts a portion of a conventional dialysis machine plus a slight modification to host a sensor coupled with the dialysate circuit, FIG. 2 Graph with the spKt/V guideline, FIG. 3 Graph with the eKt/V guideline and FIG. 4 One of the possible graphic implementations of a warning system, which notifies the user whether or not a preset goal Kt/V will be achieved at the end of the dialysis treatment.

FIG. 1 shows a draw of the dialysate circuit of a conventional dialysis machine plus a slight modification to host a sensor coupled with the dialysate circuit. The blood from a patient is taken out into an extracorporeal circuit, it flows through the tube 32 into the blood chamber 30 of a dialyzer and returns to the patient through the tube 31. The flow rate of the blood circuit is controlled by the blood pump 33. The dialysis fluid is made of several concentrates and water, therefore the machine disclosed in FIG. 1 comprises a water inlet 12, two concentrates inlets 16 and 18 and two concentrate pumps 17 and 19. The water flow together with the concentrates flow defines the final properties of the dialysis fluid. The conduit 20 takes the dialysis fluid to the dialysate chamber 29 of the dialyzer, which is separated from the blood chamber 30 by a semi permeable membrane. The dialysis fluid it is pumped into the dialyzer by the pump 21. A second pump 34 sucks the dialysis fluid and any ultrafiltrate removed from the blood. A bypass line 35 is arranged between the pumps 21 and 34. Several valves 26, 27 and 28 are arranged to control the dialysate flow. The conduit 36 leads the spent dialysate to a UV-sensor 37 measuring its light absorbance, the UV-sensor 37 is connected by an interface with the computer 14 which processes the measured data, the result of the data processing is displayed and/or printed by the device 15, which is connected with the computer 14 by an interface. The conduit 36 leads the spent dialysate after its measurement by the UV-sensor 37 to the drain system 13. The dotted lines 22, 24 and 25 represent an adaptation of the disclosed apparatus for hemodiafiltration treatments. The substitution fluid comes from a substitution fluid source 11, flows through the line 22 and is pumped in the blood lines of the patient by the pump 23. In case of post dilution hemodiafiltration the conduit 24 leads the substitution fluid to the venous line of the extracorporeal blood system; in case of pre dilution hemodiafiltration the conduit 25 leads the substitution fluid to the arterial line of the extracorporeal blood system; and in case of pre-post dilution hemodiafiltration both conduits 24 and 25 are used. The computer 14 controls all the elements shown on the figure by means of proper interfaces, said interfaces are not drawn for the sake of simplicity. The computer 14 gathers information about other parameters of the dialysis machine, like for example blood flow, dialysate flow and/or therapy time, these parameters together with the measured data are processed, the result tunes the Kt/V measuring functionality to assess deviations.

The UV-sensor 37 can be substituted by an Urea-sensor, in this case will the urea concentration in spent dialysate measured instead of the light absorbance. The disclosed dialysis machine is provided with several other means as is conventional. These other means are not disclosed, since they are not relevant for the operation of the present invention.

1.—Kt/V Guideline

At the beginning of the treatment, both the goal or prescribed Kt/V and the treatment time are used to work out a linear Kt/V guideline, the slope of said guideline will be compared against the slope of the delivered Kt/V at any treatment time.

Any linear function follows the form:

$$y = a \cdot x + b \quad \begin{vmatrix} \text{Where:} \\ a \text{ is the slope of the line} \\ b \text{ is the offset} \end{vmatrix}$$

Then it is possible to write:

$$\frac{Kt}{V} = a \cdot t + b \quad \begin{vmatrix} \text{Where:} \\ a \text{ is the slope of the line} \\ b \text{ is the offset} \end{vmatrix}$$

Assuming that K/V must be equal to 0 at the beginning of the treatment and equal to our goal or prescribed Kt/V at the end of the treatment, the slope "a" and the offset "b" can be calculated as follows:

$$\left. \begin{array}{l} 0 = a \cdot 0 + b \\ gKt/V = a \cdot t + b \end{array} \right\} \Rightarrow \left. \begin{array}{l} a = \frac{gKt/V}{t} \\ b = 0 \end{array} \right\}$$

Where, $gKt/V$ is the goal of $Kt/V$ $t$ is the treatment time in minutes

Special Cases: spKt/V and eKt/V

Assuming that urea is distributed in a single pool volume in the body, that urea generation rate and ultrafiltration are negligible during the session and that the ratio K/V remains constant over the dialysis, the Kt/V parameter can be expressed as follows:

$$\frac{Kt}{V} = -\ln\frac{C_t}{C_0} \quad (1)$$

Where, $C_t$ is the blood urea concentration at time $t$.

$C_0$ is the blood urea concentration at the beginning of the treatment.

However, the human body has more than one compartment. Urea is generated during the treatment and the dialysis ultrafiltration rate is significant. In order to consider these factors the guidelines recommend to express the initial "raw" Kt/V value in terms of single pool Kt/V or spKt/V using the Daugirdas second generation formula:

$$spKt/V = -\ln\left(\frac{C_t}{C_0} - 0.008 \cdot T\right) + \left(4 - 3.5 \cdot \frac{C_t}{C_0}\right) \cdot \frac{UF}{W} \quad (2)$$

or applying equation 1 on equation 2:

$$spKt/V = -\ln\left(\exp\left(\frac{Kt}{V}\right) - 0.008 \cdot T\right) + \left(4 - 3.5 \cdot \exp\left(\frac{Kt}{V}\right)\right) \cdot \frac{UF}{W} \quad (3)$$

Where:
K/V is the factor resulting from the fitting procedure.
t is therapy time in minutes.
T is therapy time in hours.
UF is ultrafiltration in litters.
W is dry weight in kilograms.

Even though the spKt/V parameter is accepted as a reliable dialysis quality indicator, it has been shown that urea rebound effects lead to significant overestimations of urea removal. It is possible to account for said effects expressing the Kt/V value in terms of equilibrated Kt/V or eKt/V using the Schneditz-Daugirdas formula:

$$eKt/V = spKt/V - \frac{0.6}{T} \cdot spKt/V + 0.03 \quad (4)$$

Where T is the therapy time in hours.

spKt/V Guideline

The procedure described to build a Kt/V guideline is also applicable to build a spKt/V guideline. The previous conditions are:

At the beginning of the treatment the spKt/V is 0.
At the end of the treatment the spKt/V must be the goal spKt/V.
Thus, $$\left.\begin{array}{l} 0 = a \cdot 0 + b \\ gKt/V = a \cdot t + b \end{array}\right\} \Rightarrow \left\{\begin{array}{l} a = \dfrac{gKt/V}{t} \\ b = 0 \end{array}\right.$$

Where, $gKt/V$ is the goal $spKt/V$ $t$ is the treatment time in minutes

Once the factors a and b are calculated the spKt/V can be worked out for every time t.

Figure 2:
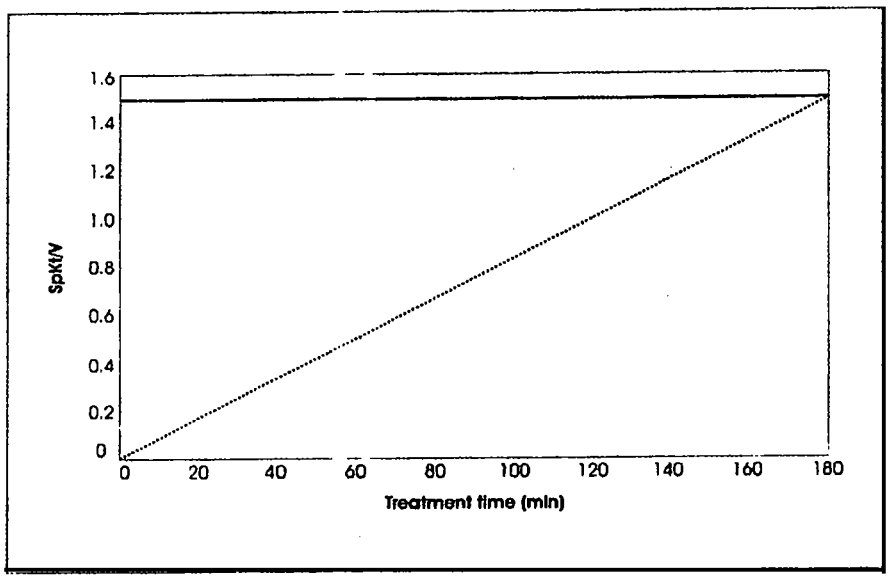

On the FIG. 2 it is possible to see a plot of the spKt/V guideline together with a line representing the delivered Kt/V.

eKt/V Guideline

The calculation of the two linear factors "a" and "b" is a bit different due to mathematical constraints on the eKt/V equation (4), meaning that the eKt/V guideline does not cross the coordinate origin but it crosses the X axe when t is about 36 minutes. The following conditions are considered in order to work out the guideline:

According to the eKt/V calculation when t is 36 minutes eKt/V is 0.03.

At the end of the treatment the eKt/V must be the goal Kt/V.
Thus, $$\left.\begin{array}{l} 0.03 = a \cdot 36 + b \\ gKt/V = a \cdot t + b \end{array}\right\} \Rightarrow \left\{\begin{array}{l} a = \dfrac{gKt/V}{t} - \left(\dfrac{0.03 \cdot t - 36 \cdot gKt/V}{t^2 - 36 \cdot t}\right) \\ b = \dfrac{0.03 \cdot t - 36 \cdot gKt/V}{t - 36} \end{array}\right.$$

Where, $gKt/V$ is the goal $eKt/V$ $t$ is the treatment time in minutes

Once the factors a and b are calculated the should Kt/V can be worked out for every time t.

According to the previous equations the eKt/V value can be negative when the time t is lower than 36, a negative Kt/V value is not possible, therefore the guideline follows the "X" axe until the eKt/V becomes positive, which is at about 36 minutes of treatment time, and then increases constantly according to the line slope, or factor a, previously calculated.

Figure 3:
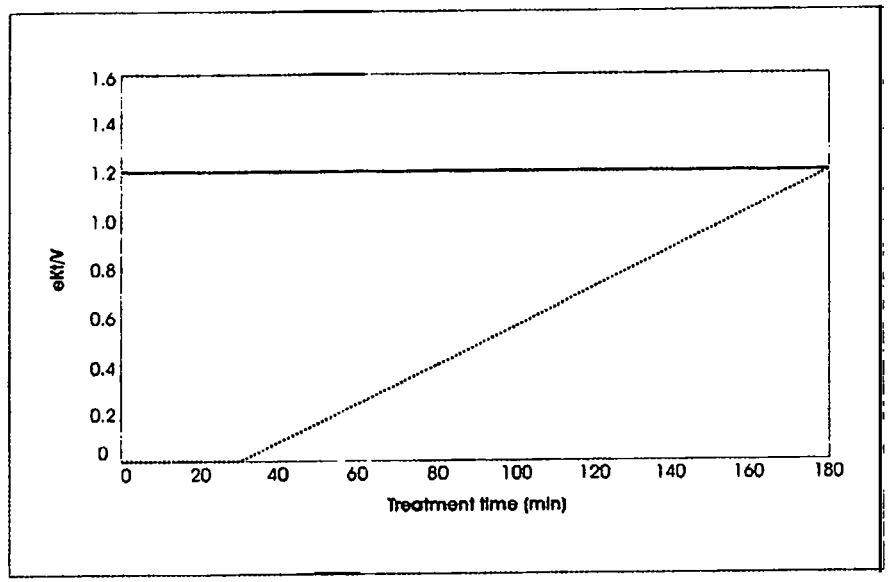

On the FIG. 3 it is possible to see a plot of the eKt/V guideline together with a line representing the delivered Kt/V.

2.—spKt/V and/or eKt/V Prediction by Analyzing the Delivered Kt/V

As it is described above, a dialysis machine equipped with a device able to measure continuously any dialysis related waste product, can measure and display an achieved Kt/V value at every treatment time. Therefore it is possible to approximate a line with slope "a" and offset "b" with the last delivered Kt/V data at every treatment time and, by the extrapolation of said line, work out the expected or predicted Kt/V at the end of the dialysis treatment.

As long as the Kt/V delivery is not constant during the whole dialysis procedure, being higher at the beginning of the treatment and lower at the end, the slope of the last Kt/V data will be also higher at the beginning and lower at the end, on the other side the slope of the Kt/V guideline is constant during the whole treatment (see above). At every treatment time the slope of the delivered Kt/V is compared with the slope of the Kt/V guideline. If the first is equal or lower than the second, the extrapolation of the delivered Kt/V line gives a good prediction of the Kt/V value at the end of the treatment.

Additionally, it is possible to implement a warning and/or alarm system, which tells the user if an eventually preset goal Kt/V will be reached or not: if the slope of the delivered Kt/V becomes lower than the slope of the Kt/V guideline, it means that both Kt/V lines meet at certain time point. If said time point lies before the end of the planned dialysis time, the goal Kt/V will not be reached.

The mathematical derivation of the above described warning system follows:

Assuming a delivered Kt/V line with slope "a" and offset "b", and a Kt/V guideline with slope "c" and offset "d":

$$Kt/V_{delivered} = a \cdot t + b$$

$$Kt/V_{guideline} = c \cdot t + d$$

If "a<c", then both lines meet at certain point and the following holds:

$$\left.\begin{array}{l} Kt/V_{delivered} = a \cdot t + b \\ Kt/V_{guideline} = c \cdot t + d \end{array}\right\} \Rightarrow a \cdot t + b = c \cdot t + d \Leftrightarrow t = \dfrac{b - d}{c - a}$$

Being t the time point where both lines meet, if said time point lies before the end of the dialysis treatment, then the goal Kt/V will not be reached.

Figure 4:
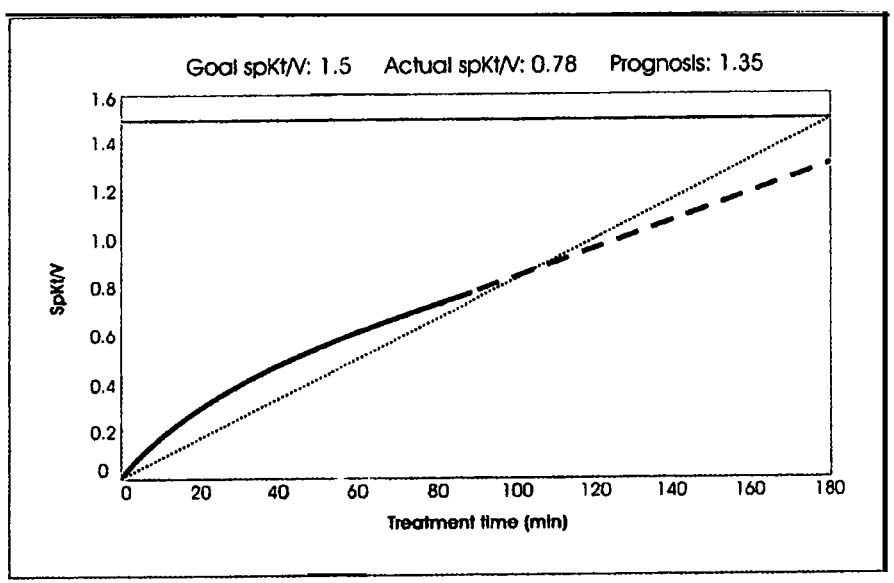

FIG. 4 depicts one of the possible graphic implementations of the above described warning and/or alarm system, where the different Kt/V values are displayed in written and graphic form:

The Kt/V prescribed by the physician or goal Kt/V is depicted by a thin horizontal solid line.

The dotted line depicts the spKt/V guideline.

The thick solid line depicts the delivered Kt/V or actual Kt/V during the first 90 minutes of treatment.

The actual Kt/V field displays the already delivered Kt/V at the current treatment time.

The thick dashed line extrapolates the delivered Kt/V line to the end of the treatment, it gives a visual idea of the expected Kt/V at the end of the treatment if the current dialysis conditions are kept constant.

The prognosis field displays the expected Kt/V at the end of the treatment if the current dialysis conditions are kept constant.

FIG. 4, shows a situation where the prescribed Kt/V will not be reached and therefore the warning system will be enabled.

3,—spKt/V and/or eKt/V Prediction by Using an Statistical Model

In another possible embodiment a prediction model based on the statistical analysis of patient data delivers a predicted value since the beginning of the treatment, when the slope of the delivered Kt/V line is greater than the one of the Kt/V guideline, and therefore the line extrapolation approach is not applicable.

The data required to build said prediction model is stored in a central database. The model is recalculated, respectively updated every time that new data comes. The way the central database is populated depends on the presence of an integrated network interface in the dialysis machine. If a network interface is absent, the treatment data must be manually downloaded and stored from the machine to the database. If a network interface is present, when the a treatment is over, an implemented software function sends the data to a network service connected with the database. Said data transfer triggers the model recalculation. Before starting the treatment, the dialysis machine requests the last updated model to the network service, the updated model is sent back to the dialysis machine and will be applied to the next treatment. The network service may be a LAN-service (Local Area Network), a WAN-service (Wide Area Network) or even a webservice.

It is also possible to store many models in the database. Said models may aim to different populations of dialysis patients and can, therefore, deliver better predictions. In such cases the machine transfers to the network service defined patient data. The network service serves back a model best suiting the patient being treated: for example models based on patient gender, age, ethnic origin, etc.

Figure 5:
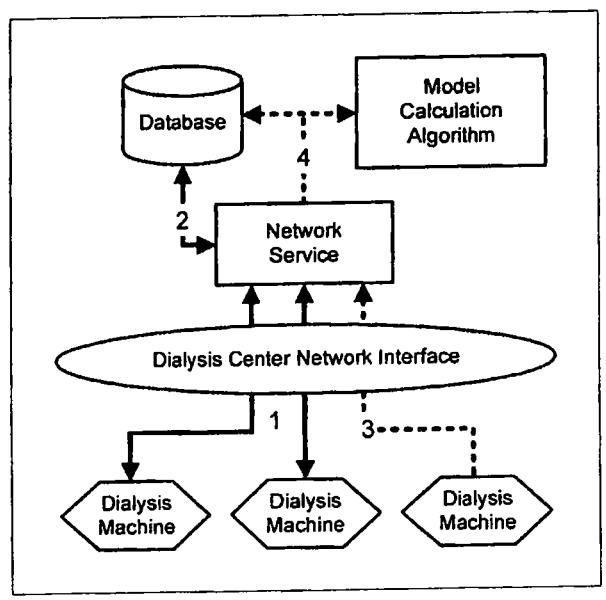
FIG. 5 Depicts a block diagram of a client-server functionality used to maintain and update prediction models for parameters evaluating the adequacy of a dialysis treatment.

FIG. 5 depicts a block diagram where this functionality is disclosed. 1 the dialysis machines request to the network service the updated model. 2 the network service requests to the database the updated model and serves it back to the dialysis machines. 3 the dialysis machine sends to the network service new treatment data. 4 the network service hands the treatment data to the database which stores it; the database interacts with the calculation algorithm to recalculate the model; the new model is stored in the database, and is therefore available for further requests of the dialysis machines.

The statistical model may include any combination of the following parameters:

a. Dialysis Machine Related Parameters:
  Achieved Kt/V, spKt/V, eKt/V, URR, spURR or eURR value.
  Alarm and/or warnings.
  Arterial bolus.
  Arterial bolus volume and flow.
  Arterial pressure on the machine's arterial pressure sensor.
  Bag weight in case of hemodiafiltration with substitution fluid in bags.
  Balance chamber ultrafiltration removal.
  Blood flow and/or blood pumps revolutions.
  Blood hematocrit.
  Blood oxygen saturation.
  Blood pressure at dialyzer inlet.
  Blood temperature.
  Concentrate pumps revolutions.
  Dialysate composition.
  Dialysate conductivity.
  Dialysate flow status of the machine: bypass or treatment.
  Dialysate flow and/or dialysate pumps revolutions.
  Dialysate temperature.
  Dialyzer's transmembrane pressure.
  Heparin bolus event and quantity of injected heparin.
  Heparin rate.
  Heparin syringe type.
  Ultrafiltration volume.
  Ultrafiltration rate.
  Used dialysis concentrates.
  UV absorbance on spent dialysate.
  Sequential dialysis periods: duration, ultrafiltrated volume and timestamp.
  Signals recorded by an UV spectrophotometer coupled with the dialysate flow system.
  Substitution fluid bolus in hemodiafiltration (HDF).
  Substitution fluid volume in HDF.
  Substitution fluid rate in HDF.
  Substitution fluid composition.
  Substitution pump revolutions.
  Therapy time.
  Type of HDF: pre-dilution, post-dilution or pre-post-dilution.
  Venous pressure on the machine's venous pressure sensor.

Any of the above listed parameters can be used with or without association with its timestamp. In case of an event, as for example an alarm, the treatment time when the event took place may be recorded and used in the prediction model. In case of a quantitative variable, the treatment time when the variable reached certain value may be recorded and used in the prediction model.

Any combination of the above listed parameters may be used on the prediction model.

Any mathematical operation using as operands any of the above listed parameters may deliver a new parameter that may be used on the prediction model.

b. Patient Related Parameters:
  Access recirculation.
  Age.
  Blood pressure during the treatment.
  Blood urea concentration pre dialysis.
  Blood urea concentration post dialysis.
  Concomitant diseases.
  Clinical history data.
  Date of first hemodialysis.
  Dialysis per week.
  Dialyzer surface.
  Dialyzer type: High flux or low flux.
  Dry weight.
  Ethnic origin.
  Glomerular filtration rate.
  Hematological disorders.
  Height.
  Kidney disease.
  Life expectancy.
  Modality of kidney substitution treatment.
  Patient's clinical history.
  Psychological status of the patient.
  Residual diuresis.
  Sex.
  Stability of the vascular access.
  Time in chronic dialysis.
  Type of vascular access.
  UV absorbance at treatment begin.
  UV absorbance at treatment end.
  Weight after dialysis.
  Weight pre dialysis.

Any combination of the above listed parameters may be used on the prediction model.

Any mathematical operation using as operands any of the above listed parameters may deliver a new parameter that may be used on the prediction model.

The prediction model may be linear or non-linear, in our preferred embodiment we use a linear model of the following form:

$$y = \beta_1 + \beta_2 \cdot \gamma_1 + \beta_3 \cdot \gamma_2 + \ldots + \beta_n \cdot \gamma_{n-1} + \epsilon$$

Where,
  y is the actual value to be estimated.
  $\beta_1, \beta_2, \ldots, \beta_n$ are the empirical factors constituting the model.
  $\gamma_1, \gamma_2, \ldots, \gamma_{n-1}$ are the variables correlating with the estimated value. In our case any of the above listed variables
  $\epsilon$ is the residual error between the actual value and the value estimated by the $\beta$ factors and $\gamma$ variables.

Our model, disclosed in the following equation, use some of the above listed parameters to predict the UV-light absorbance at the end of the treatment.

$$A(T) = \beta_1 + \beta_2 \cdot f(A_{t_1}) + \beta_3 \cdot f(UF) + \beta_4 \cdot f(G) + \beta_5 \cdot f(T) + \beta_6 \cdot f(BF) + \beta_7 \cdot f(t_1) + \beta_8 \cdot f(A_{t_1}, t_1) + \beta_9 \cdot f(T, G) + \beta_{10} \cdot f(UF, T) + \beta_{11} \cdot f(BF, G) + \beta_{12} \cdot f(UF, BF) + \beta_{13} \cdot f(A_{t_1}, T) + \beta_{14} \cdot f(A_{t_1}, G) + \varepsilon$$

Where,
A(T) is the UV-absorbance value at the end of the treatment.
Au is the first UV-absorbance measurement.
UF is the programmed ultrafiltration.
G is the patient weight before starting the treatment.
T is the planned treatment time.
BF is the programmed blood flow.
ti is the timestamp of the first absorbance measurement.
ε is the residual error between the actual value A(T) and the estimated final absorbance value.
Knowing the initial and the final predicted absorbance values allows to calculate a predicted Kt/V value by any of the following means:
Using the initial and final absorbance values by means of the following equation:

$$\frac{Kt}{V} = -\ln\left(\frac{A_t}{A_0}\right) \quad (5)$$

Given the initial and final absorbance values, a decaying exponential curve matching the urea kinetics can be generated. Different fitting procedures can be applied to the exponential curve to obtain the Kt/V value; like for example a logarithmic linearization of the curve plus a linear fit; a non-linear fit algorithm like as for example the Levenberg-Marquardt algorithm; etc. Any of the procedures can be either applied to the curve as a whole; or, to increase the accuracy, the curve may be split in subsets, on which the fitting procedures are applied, the final Kt/V will be in this case the addition of each of the subset based Kt/Vs.

Instead of estimating the final absorbance value, it is also possible to directly predict the final Kt/V value, or the final raw signal coming from the UV-sensor, which can be used to calculate the final absorbance and by extension the final Kt/V value.

4.—spKt/V and/or eKt/V Prediction by an Statistical Model in Combination with the Analysis of the Delivered Kt/V.

It is also possible to combine the statistical model described above with an analysis of the already delivered Kt/V. This approach enhances the accuracy of the prediction by using the actual treatment data to tune the initial statistical estimation.

The combination algorithm may be based on any of the in section 3 listed variables. In our preferred embodiment we base it on achieved treatment time (equation 6). The combination algorithm can work at any level: raw sensor signal, absorbance or Kt/V. In our preferred embodiment the initial estimation is weighted by a factor calculated from the analysis of the raw sensor signal. The effect of the weighting factor depends on the treatment time and increases as the treatment advances. A detailed description of the process follows:

A.—Estimation of the final absorbance value by using the statistical model described in section 3. The estimated final absorbance is expressed in terms of raw sensor signal.

B.—During the dialysis treatment, a constant monitoring of the raw sensor signal delivers an estimation, exclusively based on actual treatment data, of the expected signal at the end of the treatment.

C—Both estimations, statistical and treatment based, are combined in a final prediction. The weight that each of the components has in this final prediction depends on the treatment time. At time 0, the final prediction equals the statistical estimation; while at the end of the treatment the contribution of the statistical component is zero. The following equation describes how both components are combined:

$$Signal_{Final} = \left(1 - \left(\frac{t}{T}\right)^2\right) \cdot Signal_{Stats} + \left(\frac{t}{T}\right)^2 \cdot Signal_{Treatment} \quad (6)$$

Where t is the current treatment time and T is the total treatment time.

D.—The final prediction is expressed in terms of absorbance, and the estimated final Kt/V can be obtained, as described in the previous section, by using the initial and end absorbance values (equation 5) or by fitting a decaying exponential curve.

5.—Individualized Improvement of the Kt/V Prediction by Means of Intelligent Systems Many dialysis machines in the market offer the possibility of saving patient related parameters in a suitable media: diskette, patient card, etc. The statistical model described above can be stored on the patient card, and may be adjusted by an intelligent algorithm to better suit a given patient. The intelligent algorithm can be based on traditional feedback logic, fuzzy logic or neural networks.

Our preferred embodiment consists on a pre-existing statistical model like the one described in the previous sections. At the beginning of the therapy, the machine looks for a patient adjusted prediction model in the patient card to estimate the final absorbance value; if said adjusted model is not available the pre-existing or default model will be used. The initial estimation is then compared with the actual value achieved at the end of the dialysis. If no abnormal situations have been recorded during the treatment, like for example dialyzer clotting, access recirculation, etc; and the difference between the estimated and achieved values exceeds a certain threshold; the following actions are triggered:

A.—An accumulative occurrence parameter assessing the difference between the estimated and the achieved values during the performed therapies is calculated.

B.—An intelligent algorithm either adjusts the default prediction model or tunes the patient adjusted model.

C—The new model with updated empirical factors, namely $\beta_1, \beta_2, \ldots, \beta_{14}$, is stored back in the patient card and will be available by the next therapy.

Figure 6:
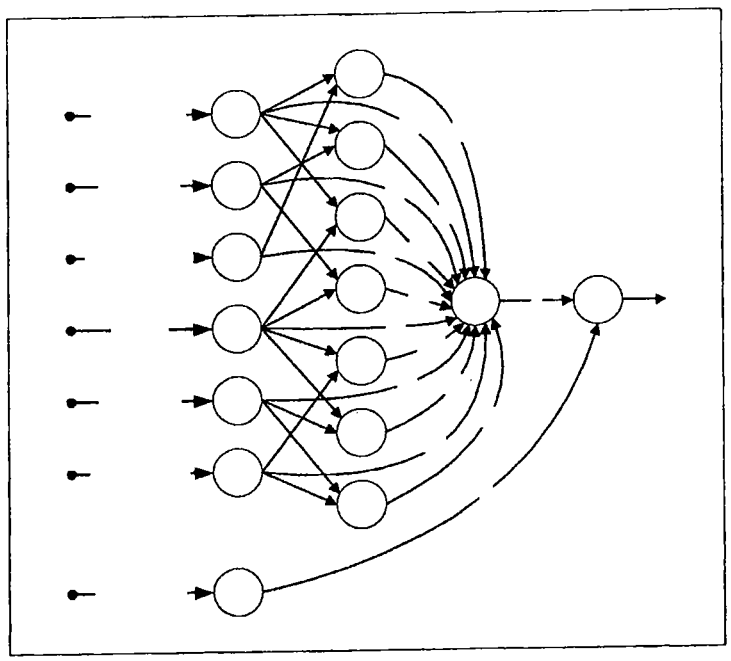
FIG. 6 Depicts one of the possible embodiments of a self-learning software system able to adjust the Kt/V prediction to the singularities of each patient.

The intelligent algorithm is a neural network (NN) with supervised training through backpropagation. The NN inputs are: the variables included in the default statistical model and the accumulative occurrence parameter. The model variables are weighted within the NN with the β factors. During the backpropagation the difference between the estimated and achieved values is minimized by adjusting the β factors. This adjustment is modulated by the occurrence factor. FIG. 6 discloses one of the possible solutions for the described neural network.

6.—Feed-Back Control of the Treatment Parameters Based on the Kt/V Prediction

As long as a reliable prediction of the Kt/V at the end of the dialysis is available, it is possible to compare at every treatment time the predicted Kt/V with the target Kt/V. A feed-back control can be implemented. Said control would use as reference or desired value the target Kt/V, as control variable the predicted Kt/V and as actuating variable any machine parameter that can have an influence on the final Kt/V. With such a system each treatment would be adjusted to the dialysis dosage that must be delivered to each patient according to the medical prescription.

The main parameters affecting the Kt/V are the blood flow, the dialysate flow, the substitution fluid flow in case of hemodiafiltration and the therapy time, therefore any variable or combination of variables having an effect on the listed parameters are suitable to become actuating variables. Among them it is important to point out the revolutions of the blood, dialysate and substitution pumps, and the software control of the treatment length based on the machine timer.

Controlling the treatment parameters to achieve the target Kt/V has the following clear advantages:
Avoids having underdialyzed patients.
Optimizes the consumption of dialysate and therefore concentrates.
Optimizes the time a patient is connected to the machine.

The invention claimed is:

1. A method for determining or predicting the adequacy parameters that will be achieved at the end of a kidney substitution treatment during said kidney substitution treatment, the method comprising the steps of:
providing the kidney substitution treatment by a machine having an extracorporeal blood system for pumping blood of a patient at a preset blood flow rate through a blood chamber of a dialyzer, the dialyzer divided by a semi-permeable membrane into the blood chamber and a dialyzing fluid chamber,
flowing the dialyzing fluid at a preset flow rate through the dialyzing fluid chamber of the dialyzer to collect waste products from the patient after flowing through the dialyzing fluid chamber of the dialyzer,
measuring continuously with a device any kidney substitution treatment related waste product to deliver together with data provided by the kidney substitution treatment machine an adequacy parameter, wherein the device is coupled with the dialyzer of the kidney substitution treatment machine, and
comparing the slope of a preferable linear guideline for the adequacy parameter, which ends at a target adequacy parameter at the end of the kidney substitution treatment, to the slope of the delivered adequacy parameter and if the slopes are equal with the next delivered adequacy parameters a linearization is performed to determine or predict the adequacy parameter at the end of the kidney substitution treatment.

2. The method according to claim 1, wherein the kidney substitution treatment is selected from a group consisting of double needle hemodialysis, single needle hemodialysis, single needle cross over hemodialysis, post-dilution hemodiafiltration, pre-dilution hemodiafiltration, pre-post- dilution hemodiafiltration, post-dilution hemofiltration, pre-dilution hemofiltration, pre- post-dilution hemofiltration, and sequential hemodialysis.

3. The method according to claim 1, wherein the adequacy parameter is selected from a group consisting of Kt/V, single pool Kt/V, and equilibrated Kt/V of any waste product present in the dialyzing fluid of the kidney substitution treatment.

4. The method according to claim 1, wherein the adequacy parameter is selected from a group consisting of the reduction ratio of any waste product present in the dialyzing fluid of the kidney substitution treatment, the single pool reduction ratio of any waste product present in the dialyzing fluid of the kidney substitution treatment, and the equilibrated reduction ratio of any waste product present in the dialyzing fluid of the kidney substitution treatment.

5. The method according to claim 1, wherein the device is a UV- Sensor.

6. The method according to claim 1, wherein the preferable linear guideline for the adequacy parameter is displayed on a user interface of the kidney substitution treatment machine.

7. The method according to claim 6, wherein the adequacy parameter represented by the guideline is selected from a group consisting of Kt/V, single pool KW, and equilibrated Kt/V of any waste product present in the dialyzing fluid of the kidney substitution treatment.

8. The method according to claim 6, wherein the adequacy parameter represented by the guideline is selected from a group consisting of the reduction ratio of any waste product present in the dialyzing fluid of the kidney substitution treatment, the single pool reduction ratio of any waste product present in the dialyzing fluid of the kidney substitution treatment, and the equilibrated reduction ratio of any waste product present in the dialyzing fluid of the kidney substitution treatment.

9. The method according to claim 3, wherein the prediction of the adequacy parameter is done by building a prediction model based on the data provided by the kidney substitution treatment machine and the device able to measure continuously any kidney substitution treatment waste product.

10. The method according to claim 9, wherein the prediction model is done by using:
at least one dialysis machine related parameter selected from a group consisting of: Achieved Kt/V, spKt/V, eKt/V, URR, spURR or eURR value, Alarm and/or warnings, Arterial bolus, Arterial bolus volume and flow, Arterial pressure on the machine's arterial pressure sensor, Bag weight in case of hemodiafiltration with substitution fluid in bags, Balance chamber ultrafiltration removal, Blood flow and/or blood pumps revolutions, Blood hematocrit, Blood oxygen saturation, Blood pressure at dialyzer inlet, Blood temperature, Concentrate pumps revolutions, Dialysate composition, Dialysate conductivity, Dialysate flow status of the machine: bypass or treatment, Dialysate flow and/or dialysate pumps revolutions, Dialysate temperature, Dialyzer's transmembrane pressure, Heparin bolus event and quantity of injected heparin, Heparin rate, Heparin syringe type, Ultrafiltration volume, Ultrafiltration rate, Used dialysis concentrates, UV absorbance on spent dialysate, Sequential dialysis periods: duration, ultrafiltrated volume and timestamp, Signals recorded by an UV spectrophotometer coupled with the dialysate flow system, Substitution fluid bolus in hemodiafiltration (HDF), Substitution fluid volume in HDF, Substitution fluid rate in HDF, Substitution fluid composition, Substitution pump revolutions, Therapy time, Type of HDF: pre-dilution, post-dilution or pre-post-dilution, and Venous pressure on the machine's venous pressure sensor,
wherein any of the dialysis machine related parameters is usable with or without association with its timestamp,
wherein in case of an event, the treatment time when the event took place may be recorded and used in the prediction model, wherein in case of a quantitative variable, the treatment time when the variable reached certain value may be recorded and used in the prediction model and any combination of the dialysis machine related parameters may be used on the prediction model any mathematical operation using as operands any of the above listed parameters may deliver a new parameter that may be used on the prediction model, and at least one patient related parameter selected from a group consisting of: Access recirculation, Age, Blood pressure during the treatment, Blood urea concentration pre dialysis, Blood urea concentration post dialysis, Concomitant diseases, Clinical history data, Date of first hemodialysis, Dialysis per week, Dialyzer surface, Dialyzer type: High flux or low flux, Dry weight, Ethnic origin, Glomerular filtration rate, Hematological disorders, Height, Kidney disease, Life expectancy, Modality of kidney substitution treatment, Patient's clinical history, Psychological status of the patient, Residual diuresis, Sex, Stability of the vascular access, Time in chronic dialysis, Type of vascular access, UV absorbance at treatment begin, UV absorbance at treatment end, Weight after dialysis, and Weight pre dialysis, wherein any combination of the patient related parameters may be used on the prediction model, and wherein any mathematical operation using as operands any of the patient related parameters may deliver a new parameter that may be used on the prediction model.

11. The method according to claim 1, wherein one or more parameters of the kidney substitution treatment are adjusted in dependence of the prediction result.

12. The method according to claim 11, wherein the adjustment of the treatment parameters is effected manually.

13. The method according to claim 11, wherein the adjustment of the treatment parameters is effected automatically.

14. The method according to claim 11, wherein the adjusted parameters include at least one of blood flow, dialysate flow and therapy time.

15. A kidney substitution treatment machine configured to implement a method for determining or predicting adequacy parameters that will be achieved at the end of a kidney substitution treatment during said kidney substitution treatment,
wherein the kidney substitution treatment machine comprises a control system,
wherein the method comprises:
providing the kidney substitution treatment by a machine having an extracorporeal blood system for pumping blood of a patient at a preset blood flow rate through a blood chamber of a dialyzer, the dialyzer divided by a semi-permeable membrane into the blood chamber and a dialyzing fluid chamber,
flowing the dialyzing fluid at a preset flow rate through the dialyzing fluid chamber of the dialyzer to collect waste products from the patient after flowing through the dialyzing fluid chamber of the dialyzer,
measuring continuously with a device any kidney substitution treatment related waste product to deliver together with data provided by the kidney substitution treatment machine an adequacy parameter, wherein the device is coupled with the dialyzer of the kidney substitution treatment machine, and
comparing with the control system the slope of a preferable linear guideline for the adequacy parameter, which ends at a target adequacy parameter at the end of the kidney substitution treatment, to the slope of the delivered adequacy parameter and if the slopes are equal with the next delivered adequacy parameters a linearization is performed to determine or predict the adequacy parameter at the end of the kidney substitution treatment,
wherein the machine is operable to allow a user to set a planned adequacy parameter at the end of the kidney substitution treatment, and
wherein an alarm or warning system is implemented to let the user know that the planned adequacy parameter at the end of the kidney substitution treatment will not be achieved.

16. A kidney substitution treatment machine according to claim 15, wherein a graphic system in combination with an alarm or warning system is implemented to let the user know that the planned adequacy parameter at the end of the kidney substitution treatment will not be achieved.

17. A kidney substitution treatment machine according to claim 15, wherein treatment data and patient data are sent to a central server by an implemented software, said central server comprising a computer connected to one of the internet, a wide area network or a local area network.

18. A kidney substitution treatment machine according to claim 15, wherein before any kidney substitution treatment the machine sends a request to a central server and gets an updated prediction model by an implemented software, wherein said central server comprises a computer connected to one of the internet, a wide area network or a local area network and wherein said updated prediction model will be used on the ensuing kidney substitution treatment to predict the adequacy parameter.

* * * * *